(12) United States Patent
Zheng et al.

(10) Patent No.: US 12,685,737 B2
(45) Date of Patent: Jul. 21, 2026

(54) ALTRENOGEST INJECTION AND PREPARATION METHOD AND USE THEREOF

(71) Applicant: NINGBO SANSHENG BIOLOGICAL TECHNOLOGY CO., LTD, Ningbo City (CN)

(72) Inventors: Xingchang Zheng, Ningbo City (CN); Sichao Zhou, Ningbo City (CN); Huanting Wu, Ningbo City (CN); Yuqiao Li, Ningbo City (CN); Yanping Liu, Ningbo City (CN); Guowei Yu, Ningbo City (CN); Xiaohong Li, Ningbo City (CN); Zhenzhen Yao, Ningbo City (CN); Jiani Shu, Ningbo City (CN); Mengyu Shao, Ningbo City (CN); Cencong Qi, Ningbo City (CN); Shiqiao Weng, Ningbo City (CN); Liming Zhou, Ningbo City (CN)

(73) Assignee: NINGBO SANSHENG BIOLOGICAL TECHNOLOGY CO., LTD, Ningbo City (CN)

( * ) Notice: Subject to any disclaimer, the term of this patent is extended or adjusted under 35 U.S.C. 154(b) by 880 days.

(21) Appl. No.: 17/911,342

(22) PCT Filed: Aug. 16, 2021

(86) PCT No.: PCT/CN2021/112859
§ 371 (c)(1),
(2) Date: Sep. 13, 2022

(87) PCT Pub. No.: WO2023/000418
PCT Pub. Date: Jan. 26, 2023

(65) Prior Publication Data
US 2024/0216393 A1 Jul. 4, 2024

(30) Foreign Application Priority Data
Jul. 19, 2021 (CN) .......................... 202110811217.0

(51) Int. Cl.
*A61K 31/567* (2006.01)
*A61K 9/00* (2006.01)
(52) U.S. Cl.
CPC .......... *A61K 31/567* (2013.01); *A61K 9/0019* (2013.01)
(58) Field of Classification Search
None
See application file for complete search history.

(56) References Cited

U.S. PATENT DOCUMENTS

| | | | | |
|---|---|---|---|---|
| 5,443,837 | A * | 8/1995 | Jobard | A61P 15/00 |
| | | | | 514/173 |
| 9,480,689 | B1 * | 11/2016 | McGlone | A61P 15/08 |
| 2001/0012844 | A1 * | 8/2001 | Shenoy | A61K 47/44 |
| | | | | 514/266.3 |
| 2012/0046518 | A1 | 2/2012 | Yoakum et al. | |
| 2017/0304260 | A1 | 10/2017 | Achacha | |
| 2020/0376002 | A1 | 12/2020 | Paolazzi | |

FOREIGN PATENT DOCUMENTS

| | | | |
|---|---|---|---|
| CN | 101522025 A | 9/2009 | |
| CN | 102291992 A | 12/2011 | |
| CN | 105816466 A | 8/2016 | |
| CN | 105878184 A | 8/2016 | |
| CN | 105919932 A | 9/2016 | |
| CN | 108042485 A | 5/2018 | |
| CN | 108403667 A | 8/2018 | |
| CN | 109260208 A | 1/2019 | |
| CN | 109464400 A | 3/2019 | |
| CN | 112137975 A | 12/2020 | |
| CN | 112587490 A | 4/2021 | |
| CN | 112641737 A | 4/2021 | |

OTHER PUBLICATIONS

Gullapalli et al. "Polyethylene glycols in oral and parenteral formulations—A critical review" 2015.*
Storer, William A., et al. "Evaluation of injectable sustained release progestin formulations for suppression of estrus and ovulation in mares." Journal of Equine Veterinary Science 29.1 (2009): 33-36.
Fan, Dehou et al., "Chinese Pharmaceutical Encyclopedia", book, Jan. 31, 1998.
He, Dong et al., Drug storage and maintenance technology, book, Aug. 31, 2009.
Li, Dongguang et al., "Practical detergent production technology manual", book, Jul. 31, 2001.

* cited by examiner

*Primary Examiner* — Danah Al-Awadi
(74) *Attorney, Agent, or Firm* — PERRY + CURRIER INC.

(57) ABSTRACT

Provided are an altrenogest injection and a preparation method and use thereof. The altrenogest injection includes 0.1-35 g altrenogest, 0.01-70 mL of polyethylene glycol, and a balance of an alcohol solvent per 100 mL of the altrenogest injection. The altrenogest injection can effectively inhibit estrus of sows, synchronize the estrus cycle of sows, and is more convenient and efficient to use, and the dosage is more precisely controllable. A single injection can effectively inhibit the estrus of sows for 6 to 12 days, which significantly reduces the labor costs for large-scale farms.

12 Claims, 4 Drawing Sheets

ALTRENOGEST INJECTION AND PREPARATION METHOD AND USE THEREOF

CROSS-REFERENCE TO RELATED APPLICATIONS

The present application claims to priority of Chinese patent application with an application number No. 202110811217.0, entitled "Altrenogest Injection and Preparation Method and Use Thereof", filed on Jul. 19, 2021 to State Intellectual Property Office of China, the entire contents of which are incorporated herein by reference.

TECHNICAL FIELD

The present application relates to the breeding technical field, and particularly to an altrenogest injection and a preparation method and use thereof.

BACKGROUND ART

Altrenogest, CAS No. 850-52-2, is a synthetic steroidal progestogen, and its chemical name is 17a-allyl-17-hydroxyestra-4,9,11-trien-3-one. Similarly to natural progesterone, the mechanism of action of altrenogest involves adjusting the estrus cycle of female animals by mainly inhibiting gonadotropin (Sitrukware, R., 2004). Altrenogest also has weak estrogenic, androgenic, and anabolic effects, and no adrenalin and anti-inflammatory effects (Feng Yanyan et al., 2020).

Oral formulations of altrenogest were first approved for marketing in France in 1984, and were developed by INTERVET INTERNATIONAL B. V. (an animal health company under Merck, also known as MSD Animal Health, referred to as "Merck") and entered the US market with FDA approval in 1990. The oral formulations of altrenogest are mainly used for regulation of the estrus cycle of horses and pigs. Generally, mares need to be fed therewith continuously for 15 days, and sows need to be fed therewith continuously for 14 or 18 days. Mares start estrus 2 to 5 days after oral administration and withdrawal, and most of them ovulate 8 to 15 days after oral administration and withdrawal. Sows enter synchronized estrus 4 to 9 days after oral administration and withdrawal (Plumb's Veterinary Drug Handbook (7th EDITION)). Currently, altrenogest has become an indispensable product for regulation of synchronization of estrus in sows in Europe and the United States, and there is no better substitute.

Currently, all the altrenogest formulations used for reproductive regulation of sows at home and abroad are oral formulations. For example, Chinese patents CN105919932A, CN108042485A, CN109260208A and U.S. Patent No. 20170304260A1 all mention oral liquid formulations of altrenogest. Chinese patents CN108403667A, CN109464400A, CN112641737A, CN112137975A and CN112587490A all mention oral solid formulations of altrenogest.

Commercially available oral altrenogest needs to be administered daily for 14 or 18 consecutive days, and there are mainly the following problems during use.

The medication cycle is long and the number of administration times is large. The frequent and large-scale administration operations in large-scale pig farms lead to increased labor costs.

Since the oral altrenogest has poor palatability and sows need a process of being familiar with and accepting feeding of oral altrenogest with a feeding gun, the sows should be domesticated with an apple juice at least 3 days before administration, so as to be fed with an altrenogest solution. Accordingly, the workload of on-site operators in large-scale pig farms is increased.

A method of administration of oral altrenogest is to spray the drug liquid on the feed and allow the sows eat freely. Such a rough administration method often causes an insufficient amount of altrenogest intake and the resulting follicular cysts in sows due to uneven spraying or splashing of the drug liquid.

Another method of administration of oral altrenogest is to directly feed the drug liquid into the oral cavity of a sow with a feeding gun. The feeding gun is repeatedly in direct contact with the oral cavity of different sows, which greatly increases risk of transmission of infectious diseases in sows.

The solvent of oral altrenogest is generally soybean oil or other oil-based solvents. Such solvents easily solidify at low temperatures. Especially in winter, the drug liquid may have greatly increased viscosity or even solidify, resulting in significant decline in convenience.

In view of the above, the present application is hereby proposed.

SUMMARY

It is an object of the present application to provide an altrenogest injection, and a preparation method and a use thereof.

The present application is implemented as follows.

In a first aspect, an embodiment of the present application provides an altrenogest injection including 0.1-35 g altrenogest, 0.01-70 mL of polyethylene glycol, and a balance of an alcohol solvent per 100 mL of the altrenogest injection.

In a second aspect, an embodiment of the present application provides a preparation method of the altrenogest injection, the method including mixing the ingredients of the altrenogest injection according to prescribed proportions.

In a third aspect, an embodiment of the present application provides a method of feeding swine, including injecting sows with the altrenogest injection according to the foregoing embodiment to synchronize the estrus cycle of the sows.

In a fourth aspect, an embodiment of the present application provide a use of the altrenogest injection according to the foregoing embodiment in the preparation of a medicament for inducing synchronization of estrus or inhibiting estrus in sows.

The present application has the following advantageous effects.

Compared with the prior art, the present application has the following advantageous effects.

The present application provides an injection-type altrenogest, which can effectively inhibit estrus of sows, synchronize the estrus cycle of sows, and increase the total number born and the number born alive, greatly improving the production efficiency of large-scale pig farms.

In addition, the altrenogest injection provided in the present application is more convenient and efficient to use, and the dosage is more precisely controllable. There is no technical problem of follicular cyst caused by insufficient intake in sows. A single injection can effectively inhibit the estrus of sows for 6 to 12 days, and there is no need for daily administration, which significantly reduces the labor costs for large-scale farms.

BRIEF DESCRIPTION OF DRAWINGS

In order to illustrate the technical solutions of the examples of the present application more clearly, the drawings to be used in the examples will be briefly introduced below. It should be understood that the following drawings merely show some examples of the present application, and therefore should not be regarded as a limitation of the scope. For those of ordinary skill in the art, other related drawings can also be obtained according to these drawings without any creative effort.

Figure 1:
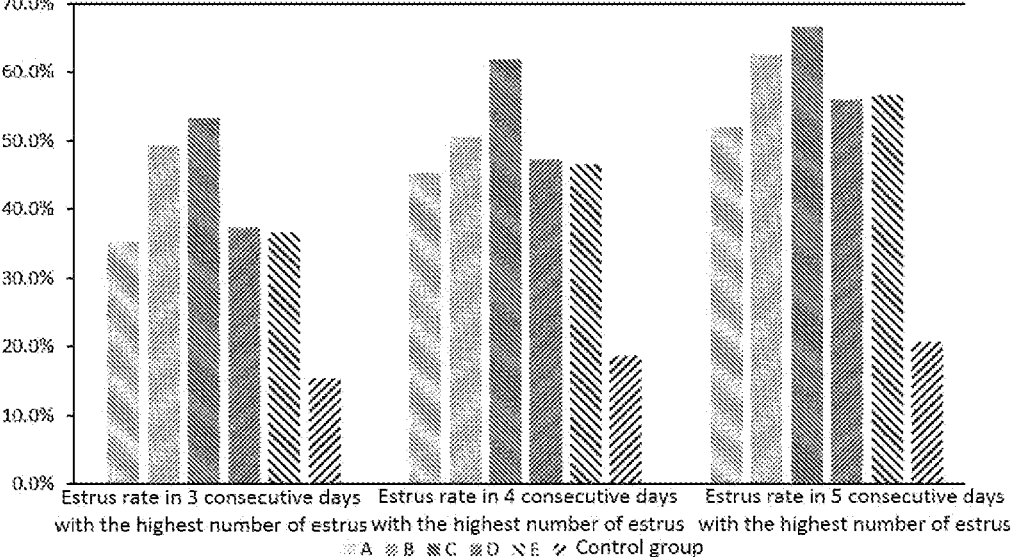
Figure 2:
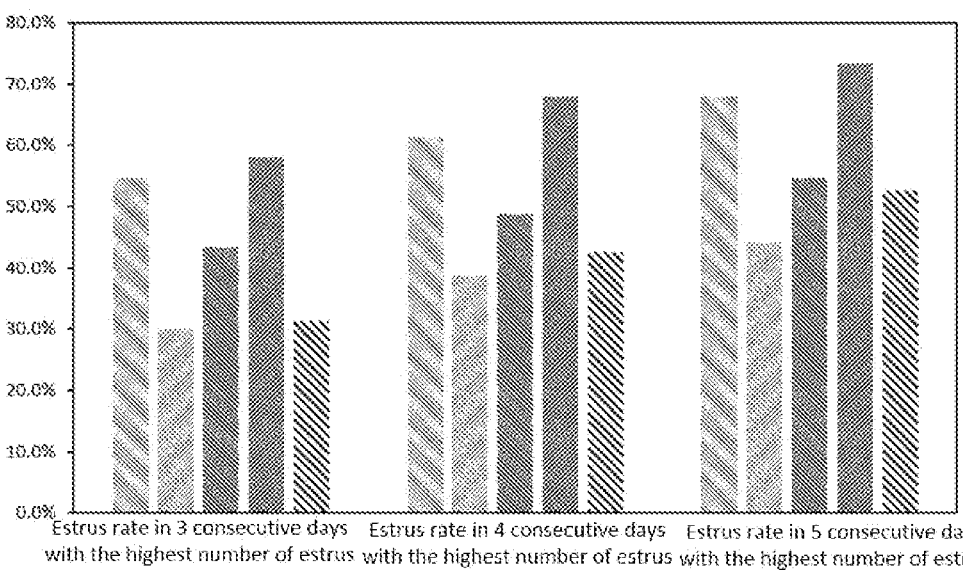
Figure 3:
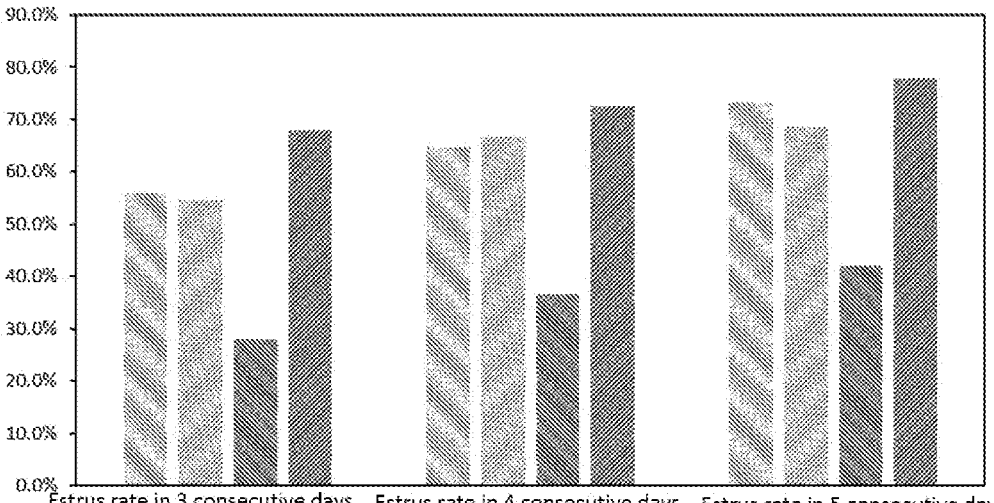
Figure 4:
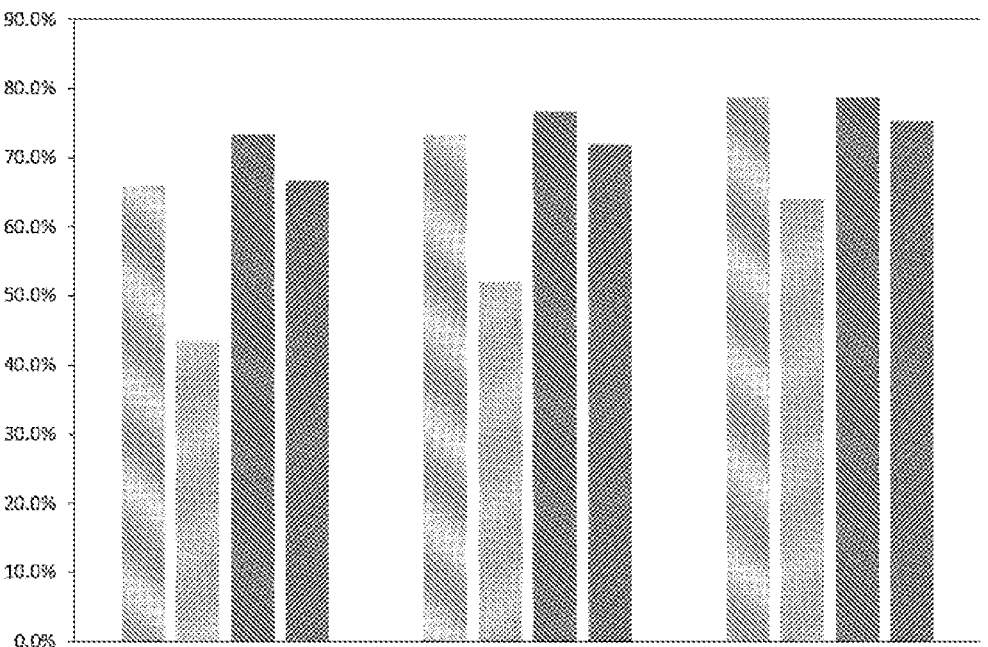
Figure 5:
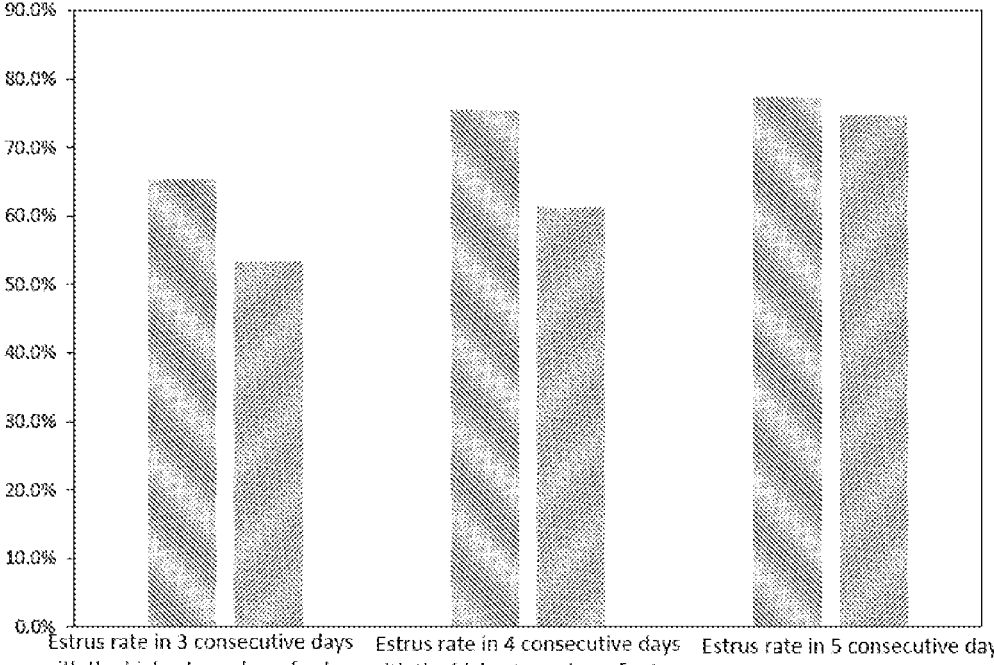
Figure 6:
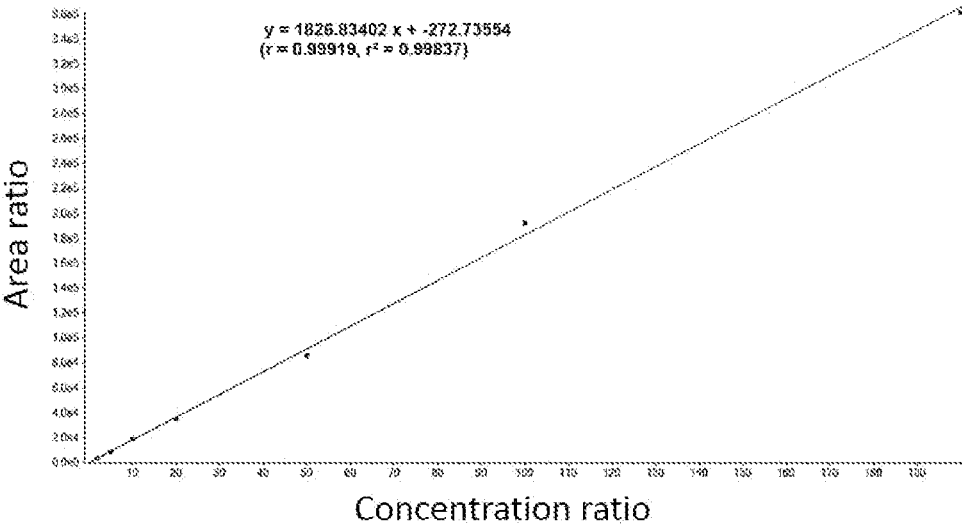
Figure 7:
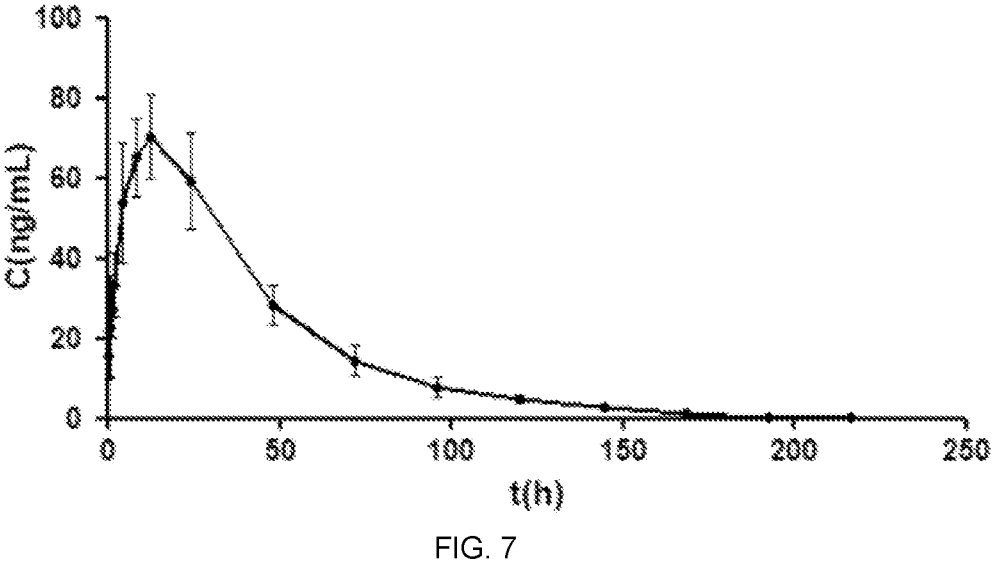
Figure 8:
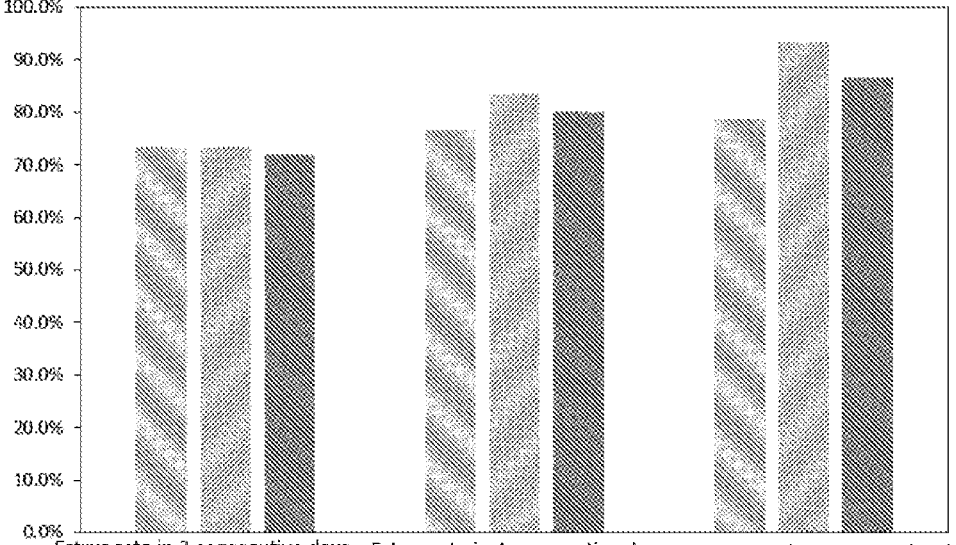

FIG. 1 shows the effect of different types of polyethylene glycol on the estrus behavior of sows in Test Example 1;

FIG. 2 shows the effect of different contents of polyethylene glycol 400 on the estrus behavior of sows in Test Example 2;

FIG. 3 shows the effect of different alcohol solvents on the estrus behavior of sows in Test Example 3;

FIG. 4 shows the effect of different concentrations of altrenogest on the estrus behavior of sows in Test Example 4;

FIG. 5 shows the effect of different administration routes on the estrus behavior of sows in Test Example 5;

FIG. 6 is a standard curve diagram of altrenogest in Test Example 6;

FIG. 7 shows the average plasma concentration-time curve (X̄±S.D, n=3) after single-dose intramuscular injection of altrenogest injection (1.5 mg/kg) in sows in Test Example 6; and FIG. 8 shows the effect of different numbers of times and intervals of administration on the estrus behavior of sows in Test Example 7.

DETAILED DESCRIPTION OF THE EMBODIMENTS

To make the objects, technical solutions, and advantages of the examples of the present application more clear, the technical solutions in the examples of the present application will be described clearly and completely below. If the specific conditions are not indicated in the examples, the examples are carried out according to the conventional conditions or the conditions recommended by the manufacturers. The used reagents or instruments without indication of the manufacturer are conventional products that can be purchased from the market.

First, an embodiment of the present application provides an altrenogest injection including: 0.1-35 g altrenogest, 0.01-70 ml of polyethylene glycol, and a balance of an alcohol solvent per 100 mL of the altrenogest injection.

Through a lot of creative works, the present application provides the above-mentioned altrenogest injection which is liquid at an ambient temperature of −20±2° C. Its mode of administration is through intramuscular or subcutaneous injection. The altrenogest injection prepared under the limitations of the above-mentioned components and their proportions can effectively inhibit the estrus of sows, synchronize the estrus cycle of sows, and increase the total number born and the number born alive, which greatly improve the production efficiency of large-scale pig farms.

Compared with the existing altrenogest used for regulating the estrus of sows, the altrenogest injection provided by the present application is more convenient and efficient to use because the needle is replaced for each administration of the altrenogest injection, and thus there is no increased risk of spread of infectious diseases of sows. The dosage is more precise and controllable, and there is no technical problem of follicular cyst caused by insufficient intake in sows. A single injection can effectively inhibit the estrus of sows for 6 to 12 days, and there is no need for daily administration, which significantly reduces the labor costs for large-scale farms.

In some embodiments, the altrenogest injection may include 0.1 g, 1 g, 2 g, 4 g, 5 g, 6 g, 8 g, 10 g, 12 g, 14 g, 16 g, 18 g, 20 g, 22 g, 24 g, 26 g, 28 g, 30 g, 32 g, 34 g or 35 g per 100 mL of the altrenogest injection.

In some embodiments, the altrenogest injection may include 0.01 mL, 0.1 mL, 1 mL, 5 mL, 10 mL, 15 mL, 20 mL, 25 mL, 30 mL, 31.5 mL, 35 mL, 40 mL, 45 mL, 50 mL, 55 mL, 60 mL, 65 mL, or 70 mL of polyethylene glycol per 100 mL of the altrenogest injection.

Preferably, the altrenogest injection may include 1-30 g altrenogest, 0.1-65 mL of polyethylene glycol, and a balance of an alcohol solvent per 100 mL of the altrenogest injection. The altrenogest injection prepared in these proportions has better and longer effect.

More preferably, the altrenogest injection may include 5-15 g altrenogest, 5-30 mL of polyethylene glycol, and a balance of an alcohol solvent per 100 mL of the altrenogest injection. These proportions can further improve the effect of the altrenogest injection.

The "polyethylene glycol" herein may be selected from known polyethylene glycol PEG, which can be obtained through existing preparation methods or purchased; and preferably, the polyethylene glycol is a PEG with a molecular weight less than 700.

Preferably, the polyethylene glycol includes at least one of polyethylene glycol 200, polyethylene glycol 300, polyethylene glycol 400, polyethylene glycol 500, and polyethylene glycol 600.

Preferably, the polyethylene glycol includes polyethylene glycol 400. When polyethylene glycol 400 is included in the polyethylene glycol, the estrus synchronization of sows has better estrus concentration.

The "alcohol solvent" herein may be selected from known alcohol solvents. Preferably, the alcohol solvent includes at least one of ethanol, 1,2-propanediol, 1,3-propanediol, isopropanol, glycerol, ethylene glycol, benzyl alcohol, phenethyl alcohol, propanol, and dipropylene glycol.

Preferably, the alcohol solvent includes at least one of ethanol, glycerol, isopropanol, and 1,2-propanediol.

More preferably, the alcohol solvent includes ethanol, glycerol, isopropanol, and 1,2-propanediol; and the volume ratio of ethanol, glycerol, isopropanol, and 1,2-propanediol is 1:(0.1-1):(0.1-1):(1-20). In some embodiments, the volume ratio of ethanol to 1,2-propanediol may be 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20; the volume ratio of ethanol to glycerol may be 1:0.1, 1:0.2, 1:0.3, 1:0.4, 1:0.5, 1:0.6, 1:0.7, 1:0.8, 1:0.9, or 1:1; the volume ratio of ethanol to isopropanol may be 1:0.1, 1:0.2, 1:0.3, 1:0.4, 1:0.5, 1:0.6, 1:0.7, 1:0.8, 1:0.9, or 1:1.

The embodiment of the present application provides a preparation method of the altrenogest injection, the method including: mixing the components of the altrenogest injection according to prescribed proportions.

Herein, "according to the proportions" refers to according to the proportions of the components of the altrenogest injection described in any of the foregoing embodiments.

Preferably, when the alcohol solvent includes ethanol, glycerol, isopropanol, and 1,2-propanediol, the preparation method includes: firstly mixing ethanol, glycerol, isopropanol, and polyethylene glycol in prescribed proportions, then adding altrenogest in a prescribed proportion and mixing them, and then adding 1,2-propanediol and mixing them to obtain a uniformly mixed semi-finished solution; and filtering the semi-finished solution through an organic microporous membrane, potting the filtered solution, sealing it with a cap, and capping, to obtain a finished product of the altrenogest injection.

The embodiment of the present application also provides a method of feeding swine, including injecting sows with the altrenogest injection according to any of the foregoing embodiments to synchronize the estrus cycle of the sows.

Preferably, a dose of the altrenogest injection is 0.1-5 mg/kg for each administration. The altrenogest injection provided by the present application can effectively inhibit the estrus of sows for a minimum of 6 days and a maximum of 12 days through a single injection; or alternatively, in order to select an appropriate estrus inhibition cycle to meet actual production demand, multiple injections are given at an interval of, for example, 8 or 9 days, and after the last injection, the sows will be intensively in estrus 11 to 14 days later.

Preferably, the sows are ones that have experienced estrus at least once.

Preferably, the mode of injection is subcutaneous injection or intramuscular injection.

Furthermore, the present application also provides a use of the altrenogest injection according to any of the foregoing embodiments in the preparation of a medicament for inducing synchronization of estrus or inhibiting estrus in sows.

Preferably, the sows are ones that have experienced estrus at least once.

The features and properties of the present application will be described in further detail below with reference to the examples.

Examples 1 to 17

Examples 1 to 17 provides altrenogest injections and preparation method thereof. The components of the altrenogest injections are basically the same, with the difference of the ingredients used in each example or their proportions, as shown in Table 1 in detail.

TABLE 1

| | | | | | | | | | | |
|---|---|---|---|---|---|---|---|---|---|---|
| | | Altrenogest injection formula | | | | | | | | |
| Group number | Example | Altrenogest (g) | Polyethylene glycol 200(ml) | Polyethylene glycol 300(ml) | Polyethylene glycol 400(ml) | Polyethylene glycol 600(ml) | Glycerol (ml) | isopropanol (ml) | Ethanol (ml) | 1,2-Propanediol (ml) |
| A | Example 1 | 5 | 10 | 0 | 0 | 0 | 5 | 5 | 15 | balance |
| B | Example 2 | 5 | 0 | 10 | 0 | 0 | 5 | 5 | 15 | balance |
| C | Example 3 | 5 | 0 | 0 | 10 | 0 | 5 | 5 | 15 | balance |
| D | Example 4 | 5 | 0 | 0 | 0 | 10 | 5 | 5 | 15 | balance |
| E | Example 5 | 5 | 2.5 | 2.5 | 2.5 | 2.5 | 5 | 5 | 15 | balance |
| F | Example 6 | 5 | 0 | 0 | 0.1 | 0 | 5 | 5 | 15 | balance |
| G | Example 7 | 5 | 0 | 0 | 5 | 0 | 5 | 5 | 15 | balance |
| H | Example 8 | 5 | 0 | 0 | 21.5 | 0 | 5 | 5 | 15 | balance |
| I | Example 9 | 5 | 0 | 0 | 65 | 0 | 5 | 5 | 15 | balance |
| J | Example 10 | 5 | 0 | 0 | 21.5 | 0 | 5 | 5 | 0 | balance |
| K | Example 11 | 5 | 0 | 0 | 21.5 | 0 | 5 | 5 | balance | 0 |
| L | Example 12 | 5 | 0 | 0 | 21.5 | 0 | 0 | 0 | 5 | balance |
| M | Example 13 | 1 | 0 | 0 | 21.5 | 0 | 0 | 0 | 5 | balance |
| N | Example 14 | 10 | 0 | 0 | 21.5 | 0 | 0 | 0 | 5 | balance |
| O | Example 15 | 30 | 0 | 0 | 21.5 | 0 | 0 | 0 | 5 | balance |
| P | Example 16 | 10 | 0 | 0 | 21.5 | 0 | balance | 0 | 0 | 0 |
| Q | Example 17 | 10 | 0 | 0 | 21.5 | 0 | 0 | balance | 0 | 0 |

7

The preparation methods of Examples 1 to 17 are basically the same. For details, refer to the preparation method of Example 1. The preparation method of Example 1 is as follows.

The components were taken according to the proportions listed in Table 1, Firstly, polyethylene glycol and an alcohol solvent (glycerol, isopropanol, and ethanol in Example 1) were added in prescribed proportions into a mixing tank, mixed evenly, and then altrenogest was added in a prescribed proportion. The mixture was stirred at a stirring speed of 200 rpm for 25 min under a dark environment. After altrenogest was completely dissolved, a balance of an alcohol solvent (1,2-propanediol in Example 1) was added to a total of 100 mL, stirring was continued at a speed of 200 rpm for 25 min to obtain a evenly mixed semi-finished solution, which is ready for use. Then, the semi-finished solution was filtered with 0.45 μm and 0.22 μm organic microporous membranes successively, followed by potting the filtered solution, sealing it with a cap, and capping, to obtain a finished product of the altrenogest injection.

Comparative Example 1

A commercially available oral solution of altrenogest (Altrenogest Oral Solution), from Ningbo Sansheng Biological Technology Co., Ltd.

8

Test Example 1: Effect of Polyethylene Glycol Type on Altrenogest Injection

Test Procedure

In this test, 900 Landrace×Large sows with 220 days of age or more, a body weight of 130 kg or more, and no obvious trauma, and having at least one estrus experience were selected. The sows were randomly assigned into 6 groups with 150 in each group. The sows were intramuscularly injected with the altrenogest injections of different compositions at a dose of 1.5 mg/kg in altrenogest content (Examples 1 to 5, test group) or 3 ml of normal saline (control group). From the $2^{nd}$ day to the $20^{th}$ day after administration, the sows were observed for estrus signs every day, and boars were used to induce estrus once in the morning and afternoon each day. The estrus identification was carried out according to the "standing reaction".

Result

The effect of different types of polyethylene glycol in the formula on the estrus behavior of sows is shown in Table 2 and FIG. 1. The significance of the data was analyzed by SPSS23 software, and the percentage data was analyzed by the $\times2$ test for statistical significance. P<0.05 indicated a significant difference.

TABLE 2

Effect of different types of polyethylene glycol in formula on estrus behavior of sows

| | | Group No. | | | | | |
| | | A | B | C | D | E | Control group |
| | | | | Number of animals | | | |
| | | 150 | 150 | 150 | 150 | 150 | 150 |
| Number of animals in estrus per day | D2 | 0 | 0 | 0 | 0 | 0 | 1 |
| | D3 | 0 | 0 | 0 | 0 | 0 | 2 |
| | D4 | 0 | 0 | 0 | 0 | 0 | 8 |
| | D5 | 0 | 0 | 0 | 0 | 0 | 5 |
| | D6 | 0 | 0 | 0 | 0 | 0 | 2 |
| | D7 | 5 | 0 | 0 | 0 | 0 | 8 |
| | D8 | 0 | 1 | 0 | 0 | 0 | 2 |
| | D9 | 2 | 0 | 4 | 0 | 3 | 0 |
| | D10 | 10 | 3 | 0 | 1 | 0 | 0 |
| | D11 | 28 | 3 | 5 | 0 | 2 | 3 |
| | D12 | 15 | 33 | 27 | 5 | 3 | 5 |
| | D13 | 15 | 22 | 28 | 26 | 15 | 15 |
| | D14 | 10 | 17 | 25 | 18 | 15 | 3 |
| | D15 | 7 | 2 | 13 | 12 | 26 | 5 |
| | D16 | 3 | 18 | 7 | 15 | 7 | 0 |
| | D17 | 5 | 3 | 2 | 13 | 22 | 1 |
| | D18 | 3 | 7 | 5 | 9 | 5 | 1 |
| | D19 | 1 | 8 | 3 | 10 | 5 | 8 |
| | D20 | 7 | 5 | 6 | 5 | 4 | 10 |
| Total number of estrus | | 111 | 122 | 125 | 114 | 107 | 79 |
| Estrus rate (%) | | 74.0%[a]* | 81.3%[b] | 83.3%[b] | 76.0%[ab] | 71.3%[a] | 52.7%[c] |
| Estrus rate in 3 consecutive days with the highest number of estrus | | 35.3%[a] | 48.0%[b] | 53.3%[b] | 37.3%[a] | 36.7% [a] | 15.3%[c] |
| Estrus rate in 4 consecutive days with the highest number of estrus | | 45.3%[a] | 50.0%[a] | 62.0%[b] | 47.3%[a] | 46.7%[a] | 18.7%[c] |
| Estrus rate in 5 consecutive days with the highest number of estrus | | 52.0%[a] | 61.3%[ab] | 66.7%[b] | 56.0%[ab] | 56.7%[ab] | 20.7%[c] |

Note:
*those marked with different letters among [a], [b], and [c] indicate significant differences in data (P < 0.05), whereas those marked with the same letter indicate no significant differences in data (P > 0.05).

It can be seen from Table 2 and FIG. 1, estrus was observed in saws on D2 in the control group, whereas estrus was observed in saws on D7, D8, D9, D10 and D9 in groups A, B, C, D and E, respectively. During the statistical period of D2 to D20, the estrus rates of all test groups were higher than those of the control group, with statistically significant difference (P<0.05). Regarding the centralized estrus rate within 3 days, the estrus rates of groups B and C were higher than those of the other groups, with statistically significant difference (P<0.05). Regarding the centralized estrus rate within 4 days, the estrus rate of group C was higher than those of the other groups, with statistically significant difference (P<0.05). Regarding the centralized estrus rate within 5 days, the estrus rates of all test groups were higher than those of the control group, with statistically significant difference (P<0.05). It can thus be seen that the altrenogest injections of Examples 1-5 of the present application can effectively inhibit the estrus of sows for a minimum of 6 days and a maximum of 9 days, and when the polyethylene glycol type in the formula was polyethylene glycol 400, the estrus synchronization of sows had better estrus concentration.

Test Example 2: Effect of Content of Polyethylene Glycol 400 on Efficacy of Altrenogest Injection Test Procedure In this test, 750 Landrace×Large sows with 220 days of age or more, a body weight of 130 kg or more, and no obvious trauma, and having at least one estrus experience were selected. The sows were randomly assigned into 5 groups with 150 in each group. The sows were intramuscularly injected with the altrenogest injections of different compositions at a dose of 1.5 mg/kg in altrenogest content (Examples 3 and 6-9). From the $2^{nd}$ day to the $20^{th}$ day after administration, the sows were observed for estrus signs every day, and boars were used to induce estrus once in the morning and afternoon each day. The estrus identification was carried out according to the "standing reaction".

Result

The effect of different amounts of polyethylene glycol 400 added in the formula on the estrus behavior of sows is shown in Table 3 and FIG. 2. The significance of the data was analyzed by SPSS23 software, and the percentage data was analyzed by the ×2 test for statistical significance. P<0.05 indicated a significant difference.

TABLE 3

Effect of different contents of polyethylene glycol 400 in formula on estrus behavior of sows

| | | Group No. | | | | |
|---|---|---|---|---|---|---|
| | | C | F | G | H | I |
| | | Number of animals | | | | |
| | | 150 | 150 | 150 | 150 | 150 |
| Number of animals in estrus per day | D2 | 0 | 0 | 0 | 0 | 0 |
| | D3 | 0 | 0 | 0 | 0 | 0 |
| | D4 | 0 | 0 | 0 | 0 | 0 |
| | D5 | 0 | 0 | 0 | 0 | 0 |
| | D6 | 0 | 0 | 0 | 0 | 0 |
| | D7 | 0 | 5 | 0 | 0 | 0 |
| | D8 | 0 | 7 | 0 | 0 | 0 |
| | D9 | 3 | 8 | 10 | 0 | 0 |
| | D10 | 0 | 15 | 7 | 0 | 0 |
| | D11 | 10 | 15 | 23 | 5 | 0 |
| | D12 | 20 | 15 | 30 | 22 | 8 |

TABLE 3-continued

Effect of different contents of polyethylene glycol 400 in formula on estrus behavior of sows

| | Group No. | | | | |
|---|---|---|---|---|---|
| | C | F | G | H | I |
| | Number of animals | | | | |
| | 150 | 150 | 150 | 150 | 150 |
| D13 | 32 | 13 | 12 | 35 | 0 |
| D14 | 30 | 7 | 8 | 30 | 5 |
| D15 | 10 | 3 | 2 | 15 | 17 |
| D16 | 5 | 7 | 3 | 8 | 10 |
| D17 | 1 | 10 | 7 | 1 | 20 |
| D18 | 5 | 5 | 5 | 3 | 17 |
| D19 | 5 | 0 | 8 | 0 | 15 |
| D20 | 3 | 1 | 5 | 5 | 8 |
| Estrus rate in 3 consecutive days with the highest number of estrus | $54.7\%^{a}$* | $30.0\%^{b}$ | $43.3\%^{c}$ | $58.0\%^{a}$ | $31.3\%^{b}$ |
| Estrus rate in 4 consecutive days with the highest number of estrus | $61.3\%^{a}$ | $38.7\%^{b}$ | $48.7\%^{b}$ | $68.0\%^{a}$ | $42.7\%^{b}$ |
| Estrus rate in 5 consecutive days with the highest number of estrus | $68.0\%^{a}$ | $44.0\%^{b}$ | $54.7\%^{c}$ | $73.3\%^{a}$ | $52.7\%^{b}$ |

Note:
*those marked with different letters among $^{a}$, $^{b}$, and $^{c}$ indicate significant differences in data (P < 0.05), whereas those marked with the same letter indicate no significant differences in data (P > 0.05).

It can be seen from Table 3 and FIG. 2 that estrus was observed in sows in groups C, F, G, H and I on D9, D7, D9, D11 and D12, respectively. During the statistical period of D2 to D20, the centralized estrus rates within 3, 4 and 5 days in groups C and H were all higher than those of the other groups, with statistically significant difference (P<0.05). Although the difference between groups C and H was not statistically significant (P>0.05), the centralized estrus rate of group H was better than that of group C in terms of numerical value.

It can thus be seen that the altrenogest injections of Examples 3 and 6-9 of the present application can effectively inhibit the estrus of saws for a minimum of 6 days and a maximum of 11 days. When the amount of polyethylene glycol 400 added per 100 ml injection was 21.5 ml, the estrus synchronization of saws had better estrus concentration.

Test Example 3: Effect of Content of Alcohol Solvent on Efficacy of Altrenogest Injection Test Procedure In this test, 600 Landrace×Large saws with 220 days of age or more, a body N weight of 130 kg or more, and no obvious trauma, and having at least one estrus experience were selected. The saws were randomly assigned into 4 groups with 150 in each group. The saws were intramuscularly injected with the altrenogest injections of different compositions at a dose of 1.5 mg/kg in altrenogest content (Examples 8 and 10-12). From the $2^{nd}$ day to the $20^{th}$ day after administration, the saws were observed for estrus signs every day, and boars were used to induce estrus once in the morning and afternoon each day. The estrus identification was carried out according to the "standing reaction".

Result

The effect of different alcohol solvents in the formula on the estrus behavior of sows is shown in Table 4 and FIG. 3.

The significance of the data was analyzed by SPSS23 software, and the percentage data was analyzed by the ×2 test for statistical significance. P<0.05 indicated a significant difference.

TABLE 4

Effect of different alcohol solvents on estrus behavior of sows

| | | Group No. | | | |
| | | H | J | K | L |
| | | | Number of animals | | |
| | | 150 | 150 | 150 | 150 |
|---|---|---|---|---|---|
| Number of animals in estrus per day | D2 | 0 | 0 | 0 | 0 |
| | D3 | 0 | 0 | 0 | 0 |
| | D4 | 0 | 0 | 0 | 0 |
| | D5 | 0 | 0 | 0 | 0 |
| | D6 | 0 | 0 | 0 | 0 |
| | D7 | 0 | 0 | 7 | 0 |
| | D8 | 0 | 0 | 0 | 0 |
| | D9 | 0 | 0 | 0 | 0 |
| | D10 | 1 | 0 | 13 | 0 |
| | D11 | 0 | 0 | 10 | 0 |
| | D12 | 15 | 2 | 15 | 22 |
| | D13 | 27 | 18 | 17 | 35 |
| | D14 | 42 | 27 | 8 | 45 |
| | D15 | 13 | 23 | 10 | 7 |
| | D16 | 13 | 32 | 10 | 8 |
| | D17 | 5 | 3 | 12 | 3 |
| | D18 | 5 | 5 | 3 | 0 |
| | D19 | 2 | 5 | 5 | 2 |
| | D20 | 3 | 2 | 1 | 1 |
| Estrus rate in 3 consecutive days with the highest number of estrus | | $56.0\%^{a}$* | $54.7\%^{a}$ | $28.0\%^{b}$ | $68.0\%^{c}$ |
| Estrus rate in 4 consecutive days with the highest number of estrus | | $64.7\%^{a}$ | $66.7\%^{a}$ | $36.7\%^{b}$ | $72.7\%^{a}$ |
| Estrus rate in 5 consecutive days with the highest number of estrus | | $73.3\%^{a}$ | $68.7\%^{a}$ | $42.0\%^{b}$ | $78.0\%^{c}$ |

Note:
*those marked with different letters among $^{a}$, $^{b}$, and $^{c}$ indicate significant differences in data (P < 0.05), whereas those marked with the same letter indicate no significant differences in data (P > 0.05).

It can be seen from Table 4 and FIG. 3 that estrus was observed in sows in groups H, J, K and L on D10, D12, D7 and D12, respectively. During the statistical period of D2 to D20, the centralized estrus rate within 3 days of group L was higher than those of the other groups, with statistically significant difference (P<0.05). The centralized estrus rate within 4 days of group K was lower than those of the other groups, with statistically significant difference (P<0.05). The centralized estrus rate within 5 days of group L was higher than those of groups J and K, with statistically significant difference (P<0.05).

It can thus be seen that the altrenogest injections of Examples 8 and 10-12 of the present application can effectively inhibit the estrus of sows for a minimum of 6 days and a maximum of 11 days. When the amount of alcohol solvent added per 100 ml of injection was 5 ml of ethanol with the balance of 1,2-propanediol, the estrus synchronization of sows had better estrus concentration.

Test Example 4: Effect of the Concentration of Altrenogest on Efficacy of Altrenogest Injection Test Procedure In this test, 600 Landrace×Large sows with 220 days of age or more, a body weight of 130 kg or more, and no obvious trauma, and having at least one estrus experience were selected. The sows were randomly assigned into 4 groups with 150 in each group. The sows were intramuscularly injected with the altrenogest injections of different compositions at a dose of 1.5 mg/kg in altrenogest content (Examples 12-15). From the $2^{nd}$ day to the $20^{th}$ day after administration, the sows were observed for estrus signs every day, and boars were used to induce estrus once in the morning and afternoon each day. The estrus identification was carried out according to the "standing reaction".

Result

The effect of different concentrations of altrenogest in the formula on the estrus behavior of sows is shown in Table 5 and FIG. 4. The significance of the data was analyzed by SPSS23 software, and the percentage data was analyzed by the ×2 test for statistical significance. P<0.05 indicated a significant difference.

TABLE 5

Effect of different altrenogest concentrations on estrus behavior of sows

| | | Group No. | | | |
| | | L | M | N | O |
| | | | Number of animals | | |
| | | 150 | 150 | 150 | 150 |
|---|---|---|---|---|---|
| Number of animals in estrus per day | D2 | 0 | 0 | 0 | 0 |
| | D3 | 0 | 0 | 0 | 0 |
| | D4 | 0 | 0 | 0 | 0 |
| | D5 | 0 | 0 | 0 | 0 |
| | D6 | 0 | 0 | 0 | 0 |
| | D7 | 0 | 0 | 0 | 5 |
| | D8 | 0 | 0 | 0 | 0 |
| | D9 | 0 | 2 | 0 | 8 |
| | D10 | 0 | 13 | 3 | 20 |
| | D11 | 0 | 27 | 0 | 53 |
| | D12 | 11 | 15 | 5 | 27 |
| | D13 | 42 | 23 | 32 | 5 |
| | D14 | 47 | 10 | 55 | 0 |
| | D15 | 10 | 21 | 23 | 5 |
| | D16 | 8 | 8 | 3 | 3 |
| | D17 | 3 | 1 | 3 | 0 |
| | D18 | 2 | 0 | 2 | 1 |
| | D19 | 1 | 3 | 5 | 3 |
| | D20 | 3 | 5 | 3 | 2 |
| Estrus rate in 3 consecutive days with the highest number of estrus | | $66.0\%^{a}$* | $43.3\%^{b}$ | $73.3\%^{a}$ | $66.7\%^{a}$ |
| Estrus rate in 4 consecutive days with the highest number of estrus | | $73.3\%^{a}$ | $52.0\%^{b}$ | $76.7\%^{a}$ | $72.0\%^{a}$ |
| Estrus rate in 5 consecutive days with the highest number of estrus | | $78.7\%^{a}$ | $64.0\%^{b}$ | $78.7\%^{a}$ | $75.3\%^{a}$ |

Note:
*those marked with different letters among $^{a}$, $^{b}$, and c indicate significant differences in data (P < 0.05), whereas those marked with the same letter indicate no significant differences in data (P > 0.05).

It can be seen from Table 5 and FIG. 4 that estrus was observed in saws in groups L, M, N and O on D12, D9, D9 and D9, respectively. During the statistical period of D2 to D20, the centralized estrus rates within 3 days and 4 days of group M were lower than those of the other groups, with statistically significant difference (P<0.05). Although the difference among groups L, N, and O was not statistically significant (P>0.05), the centralized estrus rate of group N was better than those of groups L and O in terms of numerical value. The centralized estrus rate within 5 days of group M was lower than those of the other groups, with statistically significant difference (P<0.05).

It can thus be seen that the altrenogest injections of Examples 12-15 of the present application can effectively inhibit the estrus of sows for a minimum of 6 days and a maximum of 11 days. When the amount of altrenogest added per 100 ml of injection was 10 g, the estrus synchronization of sows had better estrus concentration.

Test Example 5: Verification of Effect of Administration Route for Altrenogest Injection on Estrus Inhibition in Sows In this test, 300 Landrace×Large sows with 220 days of age or more, a body weight of 130 kg or more, and no obvious trauma, and having at least one estrus experience were selected. The sows were randomly assigned into 2 groups with 150 in each group. The two groups of sows were each intramuscularly or subcutaneously injected with the altrenogest injection of Example 14 at a dose of 1.5 mg/kg in altrenogest content. From the $2^{nd}$ day to the $20^{th}$ day after administration, the sows were observed for estrus signs every day, and boars were used to induce estrus once in the morning and afternoon each day. The estrus identification was carried out according to the "standing reaction".

Result

The effect of different administration routes on the estrus behavior of sows is shown in Table 6 and FIG. 5. The significance of the data was analyzed by SPSS23 software, and the percentage data was analyzed by the ×2 test for statistical significance. P<0.05 indicates a significant difference.

TABLE 6

Effect of different administration routes on estrus behavior of sows

| | | Group | |
|---|---|---|---|
| | | Intramuscular injection | subcutaneous injection |
| | | Number of animals | |
| | | 150 | 150 |
| Number | D2 | 0 | 0 |
| of | D3 | 0 | 0 |
| animals | D4 | 0 | 0 |
| in | D5 | 0 | 0 |
| estrus | D6 | 0 | 0 |
| per day | D7 | 0 | 0 |
| | D8 | 0 | 0 |
| | D9 | 0 | 0 |
| | D10 | 3 | 0 |
| | D11 | 15 | 0 |
| | D12 | 57 | 0 |
| | D13 | 22 | 2 |
| | D14 | 19 | 0 |
| | D15 | 3 | 20 |
| | D16 | 5 | 33 |
| | D17 | 2 | 27 |
| | D18 | 0 | 12 |
| | D19 | 1 | 20 |
| | D20 | 2 | 5 |
| Estrus rate in 3 consecutive days with the highest number of estrus | | 65.3% [a]* | 53.3% [b] |
| Estrus rate in 4 consecutive days with the highest number of estrus | | 75.3% [a] | 61.3% [b] |

TABLE 6-continued

Effect of different administration routes on estrus behavior of sows

| | Group | |
|---|---|---|
| | Intramuscular injection | subcutaneous injection |
| | Number of animals | |
| | 150 | 150 |
| Estrus rate in 5 consecutive days with the highest number of estrus | 77.3% | 74.7% |

Note:
* those marked with different letters among [a], [b], and c indicate significant differences in data (P < 0.05), whereas those marked with the same letter indicate no significant differences in data (P > 0.05).

It can be seen from Table 6 and FIG. 5 that estrus was observed in sows in the intramuscular injection group and the subcutaneous injection group on D10 and D13, respectively. During the statistical period of D2 to D20, the centralized estrus rates within 3 days and 4 days of the intramuscular injection group were both higher than those of the subcutaneous injection group, with statistically significant difference (P<0.05). For the centralized estrus rate within 5 days, the difference between the two groups was not statistically significant (P>0.05). It can thus be seen that the intramuscular and subcutaneous injection of the altrenogest injection of Example 14 of the present application can effectively inhibit the estrus of sows for 9 days and 12 days, respectively. When administration was conducted through intramuscular injection, the estrus synchronization of sows had better estrus concentration.

Test Example 6: Pharmacokinetic Test of Altrenogest Injection

The object of this test is to investigate the pharmacokinetics following a single injection of altrenogest Injection.

Test Procedure

In this test, 3 Landrace×Large sows with 220 days of age or more, a body weight of 130 kg or more, and no obvious trauma, and having at least one estrus experience were selected. The sows were intramuscularly injected with the altrenogest injection of Example 14 at a single dose of 1.5 mg/kg in altrenogest content. A blank blood sample was collected before administration, and 5 ml of blood was each collected at 10 min, 30 min, 1 h, 2 h, 4 h, 8 h, 12 h, 24 h, 48 h, 72 h, 96 h, 120 h, 144 h, 168 h, 192 h, 216 h, and 240 h after administration. The blood samples were centrifuged at 4000 rpm. The plasma was collected into a brown EP tube and frozen at −20° C. for testing. The concentration of altrenogest in plasma was determined and analyzed by high performance liquid chromatography-mass spectrometry (HPLC-MS/MS). Chromatographic peak area of altrenogest for each sample was recorded, and the concentration of altrenogest in plasma was calculated following the standard curve and regression equation. The mean value and standard deviation of measured plasma altrenogest concentrations at each time point and the concentration-time curve was plotted. The relevant pharmacokinetic parameters were calculated using WinNonlin pharmacokinetic analysis software, and the critical pharmacokinetic parameters (AUC, tmax, Cmax, etc.) were obtained.

Result

Establishment of the standard curve. 8 blank plasma samples were taken, 0.45 mL for each. 0.05 mL of a standard working solution of a respective concentration was added to achieve plasma concentrations of 0, 2, 5, 10, 20, 50, 100, and 200 ng/mL, respectively. 0.5 mL of acetonitrile was added, and the sample was vortexed for 30 s, sonicated for 10 min, centrifuged at 10000 r/min for 10 min. The supernatant was passed through a 0.22 μm organic filter membrane for HPLC-MS/MS detection. The results are shown in Table 7 and FIG. 6.

TABLE 7

Standard curve of altrenogest

| Theoretical value (ng/mL) | Back-calculated value (ng/mL) | Accuracy (%) |
|---|---|---|
| 2 | 2.055 | 102.8 |
| 5 | 4.817 | 96.3 |
| 10 | 10.564 | 105.6 |
| 20 | 19.344 | 96.7 |
| 50 | 47.150 | 94.3 |
| 100 | 105.383 | 105.4 |
| 200 | 197.666 | 98.8 |

According to the standard curve, the concentration of altrenogest in sow plasma was detected, and the detection results are shown in Table 8. The concentration-time curve is shown in FIG. 7.

TABLE 8

Plasma concentrations in sows after single-dose intramuscular injection of altrenogest injection (1.5 mg/kg)

| Sampling time(h) | Plasma concentration (ng/mL) | | | | |
|---|---|---|---|---|---|
| | 1 | 2 | 3 | $\overline{X}$ | S.D |
| 0.17 | 14.904 | 22.323 | 10.164 | 15.797 | 6.128 |
| 0.5 | 15.194 | 37.558 | 16.107 | 22.953 | 12.657 |
| 1 | 21.682 | 34.784 | 25.079 | 27.182 | 6.799 |
| 2 | 29.649 | 42.394 | 27.656 | 33.233 | 7.996 |

TABLE 8-continued

Plasma concentrations in sows after single-dose intramuscular injection of altrenogest injection (1.5 mg/kg)

| Sampling time(h) | Plasma concentration (ng/mL) | | | | |
|---|---|---|---|---|---|
| | 1 | 2 | 3 | $\overline{X}$ | S.D |
| 4 | 36.685 | 60.282 | 64.596 | 53.854 | 15.025 |
| 8 | 55.019 | 73.983 | 66.286 | 65.096 | 9.538 |
| 12 | 58.585 | 79.31 | 73.153 | 70.349 | 10.643 |
| 24 | 46.446 | 69.945 | 61.325 | 59.239 | 11.888 |
| 48 | 23.658 | 33.657 | 27.544 | 28.286 | 5.041 |
| 72 | 11.045 | 18.694 | 13.869 | 14.536 | 3.868 |
| 96 | 5.502 | 10.283 | 7.29 | 7.692 | 2.416 |
| 120 | 4.478 | 5.79 | 3.871 | 4.713 | 0.981 |
| 144 | 2.562 | 3.434 | 2.526 | 2.841 | 0.514 |
| 168 | 1.223 | 2.107 | 0.793 | 1.374 | 0.670 |
| 192 | 0.598 | 0.604 | 0.533 | 0.578 | 0.039 |
| 216 | 0.295 | 0.274 | 0.281 | 0.283 | 0.011 |
| 240 | ND | ND | ND | ND | ND |

Note:
ND means not determined.

In this test, the peak time for a single dose intramuscular injection of altrenogest oral solution in sows was about 12 h, the peak concentration $C_{max}$ was 70.349±8.690 ng/mL, the area under the concentration-time curve $AUC_{0-t}$ was 3578.636±566.380 h·ng/mL, $AUC_{0-\infty}$ was 3589.965±568.180 h·ng/mL, the half-life t½ was 24.691±0.957 h, the plasma clearance CL was 428.666±68.992 mL/h, the apparent volume of distribution V was 15175.455±1846.162 mL, and the average residence time MRT was 40.572±1.547 h. See Table 9 for details.

TABLE 9

Main pharmacokinetic parameters after single-dose intramuscular injection of altrenogest injection (1.5 mg/kg) in sows

| No. | $t_{max}$ (h) | $C_{max}$ (ng/ml) | $AUC_{0-t}$ (h · ng/ml) | $AUC_{0-\infty}$ (h · ng/ml) | $t_{1/2}$ (h) | CL (mL/h) | V (mL) | MRT (h) |
|---|---|---|---|---|---|---|---|---|
| 1 | 12 | 58.585 | 2886.730 | 2896.672 | 23.396 | 517.836 | 17478.617 | 41.324 |
| 2 | 12 | 79.310 | 4274.058 | 4288.394 | 25.680 | 349.781 | 12958.953 | 41.976 |
| 3 | 12 | 73.153 | 3575.121 | 3584.829 | 24.998 | 418.380 | 15088.796 | 38.417 |
| $\overline{X}$ | 12 | 70.349 | 3578.636 | 3589.965 | 24.691 | 428.666 | 15175.455 | 40.572 |
| S.D | 0 | 8.690 | 566.380 | 568.180 | 0.957 | 68.992 | 1846.162 | 1.547 |

In this test, the peak time for a single dose intramuscular injection of altrenogest injection in sows was about 12 h, the maximum plasma concentration was 70.349±8.690 ng/mL, and the half-life was 24.691±0.957 h. The above results showed that the altrenogest injection was slowly released after intramuscular injection. The plasma concentration maintained a stable release state for a long period of time, and the plasma concentration can be maintained at 2 ng/ml or higher within 144 h after administration. Thus, the altrenogest injection had a sustained release effect.

Test Example 7: Effect of Numbers of Times of Administration of Altrenogest Injection on Estrus Inhibition in Sows Test Procedure In this test, 450 Landrace×Large sows with 220 days of age or more, a body weight of 130 kg or more, and no obvious trauma, and having at least one estrus experience were selected. The sows were randomly assigned into 3 groups with 150 in each group. The sows were intramuscularly injected with the altrenogest injection of Example 14 at a dose of 1.5 mg/kg in altrenogest content. Group I was injected only once (D1), group II was given the $2^{nd}$ injection on D8 after the $1^{st}$ injection (D1), and group Ill was given the $2^{nd}$ injection on D9 after the $1^{st}$ injection (D1). From the $7^{th}$ day to the $25^{th}$ day after the first administration, the sows were observed for estrus signs every day, and boars were used to induce estrus once in the morning and afternoon each day. The estrus identification was carried out according to the "standing reaction".

Result

The effect of different numbers of times and intervals of administration on the estrus behavior of sows is shown in Table 10 and FIG. 8. The significance of the data was analyzed by SPSS23 software, and the percentage data was analyzed by the ×2 test for statistical significance. P<0.05 indicated a significant difference.

TABLE 10

Effects of different numbers of times and intervals of administration on estrus behavior of sows

| | | Group No. | | |
| --- | --- | --- | --- | --- |
| | | I | II | III |
| | | | Number of animals | |
| | | 150 | 150 | 150 |
| Number of animals in estrus per day | D7 | 0 | 0 | 0 |
| | D8 | 0 | 0 | 0 |
| | D9 | 1 | 0 | 0 |
| | D10 | 0 | 0 | 0 |
| | D11 | 5 | 0 | 0 |
| | D12 | 43 | 0 | 0 |
| | D13 | 40 | 0 | 0 |
| | D14 | 27 | 0 | 0 |
| | D15 | 3 | 0 | 0 |
| | D16 | 2 | 1 | 0 |
| | D17 | 7 | 0 | 0 |
| | D18 | 0 | 15 | 5 |
| | D19 | 3 | 47 | 0 |
| | D20 | 0 | 48 | 12 |
| | D21 | 5 | 15 | 40 |
| | D22 | 2 | 15 | 45 |
| | D23 | 5 | 3 | 23 |
| | D24 | 3 | 2 | 10 |
| | D25 | 1 | 0 | 7 |

TABLE 10-continued

Effects of different numbers of times and intervals of administration on estrus behavior of sows

| | Group No. | | |
| --- | --- | --- | --- |
| | I | II | III |
| | | Number of animals | |
| | 150 | 150 | 150 |
| Estrus rate in 3 consecutive days with the highest number of estrus | 73.3% | 73.3% | 72.0% |
| Estrus rate in 4 consecutive days with the highest number of estrus | 76.7% | 83.3% | 80.0% |
| Estrus rate in 5 consecutive days with the highest number of estrus | 78.7% [a]* | 93.3% [b] | 86.7% [ab] |

Note:
* those marked with different letters among [a], [b], and c indicate significant differences in data (P < 0.05), whereas those marked with the same letter indicate no significant differences in data (P > 0.05).

It can be seen from Table 10 and FIG. 8 that estrus was observed in saws in groups I, II and III on D9, D16 and D18, respectively. During the statistical period of D7 to D25, regarding the centralized estrus rate within 3 days, the difference among the groups was not statistically significant (P>0.05); regarding the centralized estrus rate within 4 days, the difference among the groups was not statistically significant (P>0.05), but group II was better than the other two groups in terms of numerical value; regarding the centralized estrus rate within 5 days, group II was higher than group I, with statistically significant difference (P<0.05), and although the difference between group Ill and group I was not statistically significant (P>0.05), group Ill was better than group I in terms of numerical value. It can thus be seen that the altrenogest injection of Example 14 of the present application in a single dose can effectively inhibit the estrus of sows for 8 days, and 2 consecutive injections at an interval of 8 days can effectively inhibit the estrus of sows for 15 days, and 2 consecutive injections at an interval of 9 days can effectively inhibit the estrus of sows for 17 days. In a case of 2 consecutive injections at an interval of 8 days, the estrus synchronization of sows had better estrus concentration.

Test Example 8: Effect of Altrenogest Injection on Reproductive Performance of Sows Test Procedure In this test, 450 Landrace×Large sows with 220 days of age or more, a body weight of 130 kg or more, and no obvious trauma, and having at least one estrus experience were selected. The sows were randomly assigned into 3 groups with 150 in each group. The sows were intramuscularly injected with the altrenogest injections of different compositions at a dose of 1.5 mg/kg in altrenogest content (Example 14, injection test group), or fed with the oral solution of altrenogest at 20 mg/animal in altrenogest content for consecutive 14 days (oral test group), or injected intramuscularly with 3 ml of normal saline (control group), and the $2^{nd}$ injection was performed on the $8^{th}$ day after the first injection (D1). From the $14^{th}$ day to the $25^{th}$ day after the first administration for the injection test group and the oral test group, and from the $3^{rd}$ day to the $25^{th}$ day after the first administration for the control group, the sows were observed for estrus signs every day, and boars were used to induce estrus once in the morning and afternoon each day.

The estrus identification was carried out according to the "standing reaction". If the standing reaction appears, an insemination operation was performed at an interval of 8-12 hours, and then a second insemination operation was performed at an interval of 8-12 hours. If no standing reaction appears, boars were used again to induce estrus on the next day. During the period of test, the number of bred sows was recorded, and the number of pregnant sows was checked by B-ultrasound 28-35 days after the second breeding. In addition, the number of farrowing sows and the number of healthy piglets and litter size of farrowing sows were recorded. Adverse reactions at the injection site were recorded during the test.

Result

The effect of altrenogest injection on the reproductive performance of sows is shown in Table 11. The significance of the data was analyzed by SPSS23 software, and the percentage data was analyzed by the ×2 test for statistical significance. P<0.05 indicated a significant difference.

Example 1 was taken and poured into a 50 ml beaker, and the beaker was sealed with parafilm. First, the beakers containing the liquid was placed in a 25±2° C. environment for 5 hours, the parafilm was torn off. The properties of the liquid was tested using a glass rod, and the change of properties of the liquid was recorded. The beaker containing the liquid was sealed again, placed in a −20±2° C. environment for 5 hours, and the parafilm was torn off. The properties of liquid were tested with a glass rod, and the change of properties of the liquid was recorded. When the liquid was stirred with the glass rod, the state where the rod can be inserted into the liquid naturally by gravity and no crystals were precipitated is considered to be in a liquid form. When the liquid was stirred with the glass rod, the state where the rod cannot be inserted into the liquid naturally by gravity and crystals were precipitated is considered to be in a solid form.

TABLE 11

Effect of altrenogest injection on reproductive performance of sows

| Group No. | Number of animals | Breeding rate(%) | Conception rate(%) | Farrowing rate(%) | Average number of healthy piglets (animals) | Average litter size (animals) | Reproductive efficiency (animals) |
|---|---|---|---|---|---|---|---|
| Injection test group | 150 | 93.3[a]* | 94.6 | 98.1 | 11.35 ± 1.64 [a] | 12.21 ± 1.93 [a] | 1134 |
| Oral test group | 150 | 95.0[a] | 91.2 | 100.0 | 11.56 ± 1.48 [a] | 12.15 ± 1.55 [a] | 1108 |
| Control group | 150 | 71.7[b] | 93.0 | 95.0 | 10.31 ± 1.64 [b] | 11.16 ± 1.49 [b] | 986 |

Note:

*those marked with different letters among [a], [b], and c indicate significant differences in data (P < 0.05), whereas those marked with the same letter indicate no significant differences in data (P > 0.05);

In the table: breeding rate = number of bred animals/number of test animals * 100%;

Conception rate = number of pregnant animals confirmed by B-ultrasound/number of bred animals * 100%;

Farrowing rate = number of farrowing animals/number of pregnant animals confirmed by B-ultrasound * 100%;

Reproductive efficiency = (number of farrowing animals/number of bred animals) × 100 × Average litter size.

It can be seen from Table 11 that there was no statistically significant difference in the breeding rate, conception rate, farrowing rate, average number of healthy piglets and average litter size between the injection test group and the oral test group (P>0.05). In the comparison of the control group with the test group (injection test group and oral test group), the breeding rate, average number of healthy piglets, and average litter size were statistically significant (P<0.05), except the conception rate and farrowing rate. The reproductive efficiency of the test group was higher than that of the control group. It can thus be seen that the altrenogest injection of Example 14 of the present application can effectively improve the reproductive performance of the sows like the altrenogest oral solution. No adverse reaction was observed at the injection site during the test.

The above results showed that the altrenogest injection of the present application can safely and effectively improve the reproductive performance of sows.

Test Example 9: Comparative Test of Change of Properties of Altrenogest Injection and Altrenogest Oral Solution Under Low Temperature Environment Test Procedure 25 ml of each of the altrenogest injections of Examples 1-17 and the altrenogest oral solution of Comparative Result The effect of different ambient temperatures on the properties of altrenogest injection and altrenogest oral solution is shown in Table 12.

TABLE 12

Effect of different ambient temperatures on the properties of altrenogest injection and altrenogest oral solution

| Group No. | Properties of liquid | |
|---|---|---|
| | 25 ± 2° C. | −20 ± 2° C. |
| A | liquid | liquid |
| B | liquid | liquid |
| C | liquid | liquid |
| D | liquid | liquid |
| E | liquid | liquid |
| F | liquid | liquid |
| G | liquid | liquid |
| H | liquid | liquid |
| I | liquid | liquid |
| J | liquid | liquid |
| K | liquid | liquid |
| L | liquid | liquid |
| M | liquid | liquid |
| N | liquid | liquid |
| O | liquid | liquid |

TABLE 12-continued

Effect of different ambient temperatures on the properties
of altrenogest injection and altrenogest oral solution

| Group No. | Properties of liquid | |
| --- | --- | --- |
| | 25 ± 2° C. | −20 ± 2° C. |
| P | liquid | liquid |
| Q | liquid | liquid |
| Comparative Example 1 | liquid | solid |

It can be seen from Table 12 that the commercially available altrenogest oral solution changed significantly from a liquid form to a solid form under low temperature environment, whereas the altrenogest injection of the present application can still maintain the liquid form possessed at a normal temperature condition even under low temperature environment. Therefore, when the altrenogest injection of the present application is used in a cold area, the liquid can be kept from solidification, and its convenience of use is greatly enhanced.

The above descriptions are only preferred examples of the present application, and are not intended to limit the present application. For those skilled in the art, various modifications and changes can be made to the present application. Any modification, equivalent replacement, improvement, and the like made within the spirit and principle of the present application shall be included within the protection scope of the present application.

INDUSTRIAL APPLICABILITY

The present application provides an injection-type altrenogest, which can effectively inhibit estrus of sows, synchronize the estrus cycle of sows, and increase the total number born and the number born alive, greatly improving the production efficiency of large-scale pig farms. The altrenogest injection provided in the present application is more convenient and efficient to use, and the dosage is more precisely controllable. There is no technical problem of follicular cyst caused by insufficient intake in sows. A single injection can effectively inhibit the estrus of sows for 6 to 12 days, and there is no need for daily administration, which significantly reduces the labor costs for large-scale farms.

The invention claimed is:

1. A method of feeding swine, comprising injecting sows with an altrenogest injection to synchronize an estrus cycle of the sows, wherein the altrenogest injection comprises 0.1-35 g altrenogest, 0.01-70 ml of at least one polyethylene glycol, and a balance of at least one alcohol solvent per 100 mL of the altrenogest injection.

2. The method of feeding swine according to claim 1, wherein a dose of the altrenogest injection is 0.1-5 mg/kg for each administration.

3. The method of feeding swine according to claim 2, wherein the sows are ones that have experienced estrus at least once.

4. The method of feeding swine according to claim 2, wherein an injection mode of the altrenogest injection is intramuscular injection or subcutaneous injection.

5. The method according to claim 1, wherein the altrenogest injection comprises 1-30 g the altrenogest, 0.1-65 mL of the at least one polyethylene glycol, and a balance of the at least one alcohol solvent per 100 mL of the altrenogest injection.

6. The method according to claim 5, wherein the altrenogest injection comprises 5-15 g the altrenogest, 5-30 ml of the at least one polyethylene glycol, and a balance of the at least one alcohol solvent per 100 ml of the altrenogest injection.

7. The method according to claim 1, wherein the at least one polyethylene glycol is PEG with a molecular weight less than 700.

8. The method according to claim 1, wherein the at least one polyethylene glycol is selected from the group consisting of polyethylene glycol 200, polyethylene glycol 300, polyethylene glycol 400, polyethylene glycol 500, and polyethylene glycol 600.

9. The method according to claim 8, wherein the at least one polyethylene glycol comprises the polyethylene glycol 400.

10. The method according to claim 1, wherein the at least one alcohol solvent is selected from the group consisting of ethanol, 1,2-propanediol, 1,3-propanediol, isopropanol, glycerol, ethylene glycol, benzyl alcohol, phenethyl alcohol, propanol, and dipropylene glycol.

11. The method according to claim 10, wherein the at least one alcohol solvent is selected from the group consisting of ethanol, glycerol, isopropanol, and 1,2-propanediol.

12. The method according to claim 11, wherein the at least one alcohol solvent consists of ethanol, glycerol, isopropanol, and 1,2-propanediol; and a volume ratio of ethanol, glycerol, isopropanol, and 1,2-propanediol is 1:0.1-1:0.1-1:1-20.

* * * * *